United States Patent
Khaled

(10) Patent No.: US 11,654,176 B1
(45) Date of Patent: May 23, 2023

(54) NUTRIENT COMPOSITION TO NORMALIZE BLOOD SUGAR AND RELATED HEALTH COMPLICATIONS

(71) Applicant: Mohammad A. Khaled, Birmingham, AL (US)

(72) Inventor: Mohammad A. Khaled, Birmingham, AL (US)

( * ) Notice: Subject to any disclaimer, the term of this patent is extended or adjusted under 35 U.S.C. 154(b) by 0 days.

(21) Appl. No.: 16/147,863

(22) Filed: Sep. 30, 2018

Related U.S. Application Data

(60) Provisional application No. 62/566,275, filed on Sep. 29, 2017.

(51) Int. Cl.

| | | |
|---|---|---|
| A61K 36/54 | (2006.01) | |
| A61K 36/48 | (2006.01) | |
| A61K 36/42 | (2006.01) | |
| A61K 36/24 | (2006.01) | |
| A61P 29/00 | (2006.01) | |
| A61K 36/185 | (2006.01) | |
| A61K 9/20 | (2006.01) | |
| A61P 3/10 | (2006.01) | |
| A61K 36/33 | (2006.01) | |

(52) U.S. Cl.
CPC ............... *A61K 36/54* (2013.01); *A61K 9/20* (2013.01); *A61K 36/185* (2013.01); *A61K 36/24* (2013.01); *A61K 36/33* (2013.01); *A61K 36/42* (2013.01); *A61K 36/48* (2013.01); *A61P 3/10* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 2012/0148685 A1* | 6/2012 | Rohner | A61K 36/82 424/727 |
| 2015/0190446 A1* | 7/2015 | Fogel | A61K 36/185 424/739 |

* cited by examiner

*Primary Examiner* — Ralph J Gitomer

(57) ABSTRACT

A composition comprising an extract of *Trigonella foenum Graecum*, Fenugreek and Cinnamon administered in high doses is capable of arresting the formation Glocotoxicity and Lipotoxicity which lead to Insulin Resistance (IR), the hall mark of Type 2 Diabetes (T2DM). Natural ingredients with similar properties to Fenugreek and Cinnamon are used in the composition to function in synergy with the Fenugreek and Cinnamon to control IR and to minimize any undesirable side effects of using the high doses of Fenugreek and Cinnamon. Use of the composition results in a significant reduction of IR with a remarkable improvement in health in subjects suffering either from pre-diabetes and/or from T2DM.

12 Claims, 1 Drawing Sheet

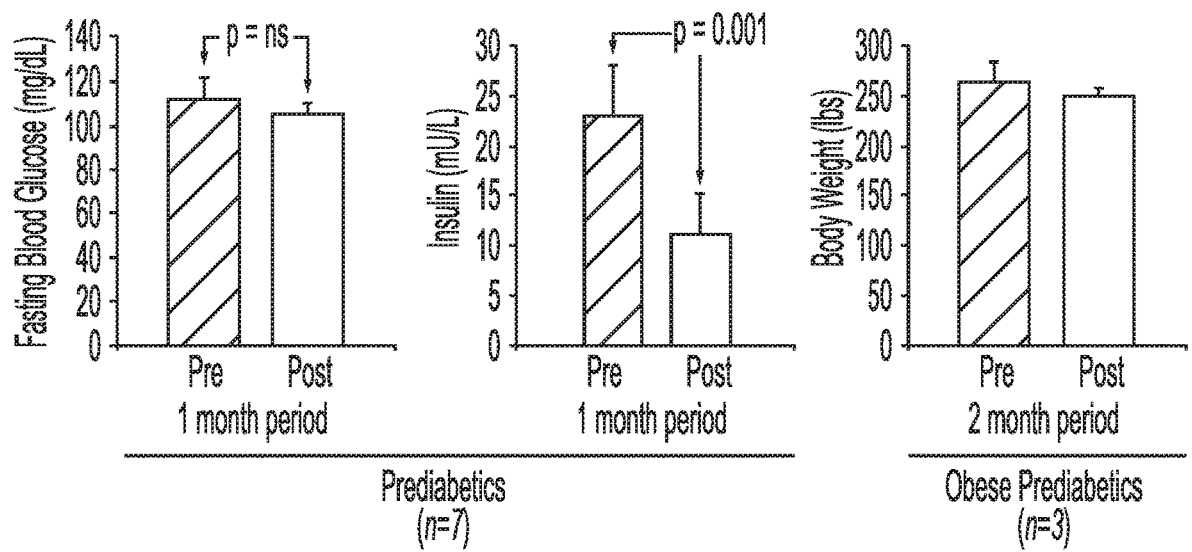

NUTRIENT COMPOSITION TO NORMALIZE BLOOD SUGAR AND RELATED HEALTH COMPLICATIONS

BACKGROUND

Diabetes is a complex metabolic disease, starting with pancreatic beta-cell dysfunctions to inactive and/or unavailable insulin receptors (IRS-1) giving rise to insulin resistance (IR), a hall mark of Type 2 Diabetes (T2DM). Most current anti-diabetic drugs target these problems, but with many side-effects and limited success. Recent research also reveals that INFLAMMATION, a culprit for most human health complications, is also intimately involved in the inactivation of glucose transporter (GLUT4) particularly in fat cells/adipose tissues by inhibiting IRS-1, thus initiating lipotoxicity, which is important in the creation of IR. Additionally, current drug therapies do NOT take into account of the detrimental interactions of circulating reactive sugar molecules, such as fructose and glucose, generating glucotoxicities from food, particularly carbohydrates. These reactive sugar molecules, i.e. glucotoxicities, react with many important enzymes and proteins leading to the formation of advance glycosylated end (AGE) products; which are intimately associated with diseases of ageing processes including T2DM. In fact, new research findings also reveal that intensive blood sugar control with hypoglycemic drugs, including insulin, have minimal effects on clinical micro- and macrovascular outcomes (Hollman R R et al. NEJM 2008; 359:1577). Once pancreatic insulin secretion is exhausted, administration of exogenous insulin is required, which is also not devoid of side-effects. These findings strongly suggest that sensitization of insulin with concomitant inactivation of reactive sugar species, particularly glucotoxicities, is important in order to successfully manage T2DM. Furthermore, diet-induced postprandial inflammation, as associated with glucotoxicities and lipotoxicities, has recently been predicted to be one of the primary risk factors for beta-cell dysfunction and insulin resistance (Klop B et al. Internat J Vascular Med 2012; doi:10.1155/2012/947417). Since postprandial inflammation usually occurs about 2 hours after consuming a meal it is critical to implement any interventions around this time in order to prevent these diet-induced toxicities (O'Keefe J H and Bell D S H. Am J Cardiol 2007; 100:899).

Natural products, belonging to traditional medicines or complementary and alternative medicines, have previously been used to treat human diseases for many years and are gaining resurgence of interest in drug development. In fact, Metformin, a popular drug to treat Type 2 diabetes (T2DM), is a biguanide derivative of guanide, which originated from the plant goat's rue (*Galega officinalis*). Interestingly, it was also found recently that a 7 gram dose of bitter melon (*Momordica charantia*) extract given to an adult human subject daily is comparable to the treatment efficacy as exerted by only 5 milligrams of the anti-diabetes drug Glibenclamide. Such a high dose of bitter melon extract not only poses odd situations for its production and human consumption, but also its long term use may very likely induce unwanted effects, as found in *Ephedra* which was once a popular weight loss product derived from a natural source. It is important to remember in this context the saying of a 16th century Swiss scientist, Paracelsus, "Poison is in everything, and nothing is without poison. The dosage makes it either a poison or a remedy". Accordingly, higher doges induce higher toxicities. It is desirable, therefore, to compose a product in combination with several ingredients, with similar properties to function in synergy, thus giving rise to an efficacious product that is virtually devoid of any unwanted side effects. So traditional medicines are usually comprised of more than one natural plant/herb extract in order to minimize any undesirable effects due to a high dose of any single ingredient. Although there is a recent surge of nutritional products, particularly in the US market, there is, however, little rigorous scientific evidence proving their efficacy, and their mode of actions are generally unknown. This is all the more evident in the management of T2DM, since most traditional medicines and nutritional products have not been found to reap the real-world clinical benefits. Therefore, an appropriate combination of proper and efficacious nutritional, natural and herbal ingredients, with a clear understanding of mechanisms of action of each of them, constituting a multi-target approach, could thus be very helpful in maintaining good health and wellness of T2DM patients.

SUMMARY OF THE INVENTION

Based on the above facts and findings 4K Nutripharma developed an effective integrated anti-inflammatory system (IAS) capable of scavenging pro-inflammatory particles which is invariably being used in most of 4K's products. Additionally, since both the gluco- and lipotoxicities have been found to be intimately involved in the initiation of insulin resistance (IR), 4K formulated a new nutrient Composition, as illustrated below, composed of novel natural/herbal/nutritional components in order to prevent the formation of IR, the hallmark of T2DM. The primary objective, in this context, was to find efficacious natural products in order to prevent both the gluco- and lipotoxicities arising soon after digesting a regular meal/food, containing mostly carbohydrates and fats/oils/lipids.

First, in search of an effective natural ingredient to inhibit glucotoxicities, *Galega officinalis* L. (Fabaceae), which is also known as Goat's rue, French lilac, or Italian fitch, a guanidine derivative, galegine, was identified. Goat's rue has been prescribed since the Middle Age to treat diabetes mellitus. Galegine from this plant, whose chemical structure is quite similar to the anti-diabetic drug Metformin, is responsible for the lowering of blood glucose produced from this plant extract (Perla V and Jayanty S S. Food Chem 2013; 138: 1574).

Second, in order to inhibit lipotoxicities, Cinnamon, *Cinnamomum cassia* Siebold (Lauraceae), is a spice being used worldwide and has been proven clinically to be a natural insulin sensitizer in adipocytes (Gruenwald J, Freder J, Armbruester N. Cinnamon and health. Crit Rev Food Sci Nutr 2010; 50: 822). In fact, recently Kashvari M et al. (Arya Atheroscler. 2013; 9:280) found that cinnamon considerably inhibited lipotoxicity related lipid peroxidation leading to anti-inflammatory effects in the human and animal body.

From the above findings it is clear that Goat's rue extract and Cinnamon extract could be very effective inhibitors against gluco- and lipotoxicities respectively. Therefore, these two natural ingredients are considered to be essential primary constituents in our new Nutrient Composition for the treatment of T2DM, as listed below in Table 1.

TABLE - 1

| INGREDIENTS | AMOUNTS | RANGES |
| --- | --- | --- |
| Goat's rue | 150 mg | 20-1,000 mg |
| Cinnamon | 225 mg | 30-1,800 mg |

A higher dose of Goat's rue, on prolong use, could have serious effects on blood circulation, while Cinnamon, similarly, may pose side-effects on lungs function (Rasekh H R et al. *J Ethnopharmacol.* 2008; 116:21 and http://www.livestrong.com/article/445647). In order to minimize these side effects, it is necessary to combine these two ingredients of Table 1 with other natural ingredients, as adjunctive, at adequate doses to provide similar therapeutic effects synergistically at lower doses. In search of such ingredients, we took into account the fact that the gluco- and lipotoxicities, as indicated earlier, usually occur in response to consuming a meal rich in carbohydrates and lipids respectively. The idea is, therefore, that these adjunctive natural ingredients should also be capable enough to prevent the absorption of sugar molecules and lipids, as generated from food while in the digestive track, thus functioning synergistically with the ingredients of Table 1. The ingredients identified in this way are described below.

Adjunctive to Goat's Rue:

1. Gymnema

The leaf of G. Sylvester is a reputed herb in both Ayurveda and Western medicines. It shows positive effects on blood sugar homeostasis and controls sugar cravings (Jiwari P et al. Biomed Res Int 2014; 2014: 830285). The active compounds have been cited such as gymnemic acids and gurmarin, showing a their effects on glucagon-like peptide 1 (GLP-1) levels in the secretion of insulin and inhibition of glucose absorption in the bowel (Di Fabio G et al. Molecules 2013; 18: 14892). Other effects of Gymnema extract include a prolonged hypoglycemic action of exogenous insulin, intensification of effects of insulin, and extended duration of reduced glucose levels. However, two small, open-label trials have also yielded promising results after administration of Gymnema to patients with T2DM. In the first trial, patients that received 200 mg daily for 18 to 20 months significantly improved fasting blood glucose. The second trial was uncontrolled, and patients that received 800 mg daily of a similar extract for 3 months reduced fasting blood glucose. In conclusion, Gymnema appears to improve glycemic control suggesting that it could be beneficial for the management of T2DM.

2. Bitter Melon

*Momordica charantia*, a Botanical name, is a climbing perennial plant that produces elongated fruits with a pronounced bitter taste, which is known as bitter melon or bitter gourd. This species has been studied in vitro and in vivo for its potential anti-diabetic properties, with different parts of this plant (seeds, fruit pulp, leaves, and whole plant) and different doses (from 400 mg to 6 g/day) being assayed (Leung L et al. Br J Nutr 2009; 102:1703). In experiments using rats, *M. charantia* improves glucose (24%) in the caper-treated group vs. control (16%). The authors concluded that Bitter Melon could be used as an adjunctive agent for the treatment of T2DM patients.

Adjunctive to Cinnamon:

Cinnamon, as indicated above, helps preventing lipotoxicities by reducing lipid peroxidation as well as preventing absorption of lipid molecules from the digestive track. Recently, Felisberto M H F et al. (LWT-Food Sci and Tech. 2015; 63:1049) demonstrated that lipid reduction from food could be achieved conveniently by using mucilage from various natural plants and vegetables, such as Flaxseeds, Chia seeds, Cacti (e.g. Nopal), Okra and many more. However, Okra and Nopal were found to be the two most effective adjunctive natural ingredients to work in synergy with Cinnamon, as described below.

1. Okra

With the scientific name as "*Abelmoschus esculentus*" and also as "*Hibiscus esculentus*" is a well known vegetable worldwide. Okra is a rich source of many nutrients, including fiber, vitamin B6 and folic acid. Okra's mucilage not only binds cholesterol but bile acid carrying toxins dumped into it by the filtering liver. This incredibly valuable vegetable not only binds excess cholesterol and toxins (in bile acids) which cause numerous health problems if not evacuated, but then assures easy passage out of the body of same. Further contributing to the health of the intestinal tract, okra fiber as well as its mucilage has no equal among fibers and mucilage for feeding the good bacteria (probiotics) by retaining most of okra's nutrients and self-digesting enzymes. Dietary supplementation with okra is effective in reducing serum glucose and lipid levels whilst improving antioxidant capacity showing the promising anti-hyperglycemic, anti-hyperlipidemic, anti-inflammatory properties (Hajian S et al. Ann Res Antioxid. 2016; 1:e23).

2. Nopal

*Opuntia ficus-indica*, commonly referred to as prickly pear or Nopal cactus, is a dicotyledonous angiosperm plant. It belongs to the Cactaceae family and is characterized by its remarkable adaptation to arid and semi-arid climates in tropical and subtropical regions of the globe. Hwang S H et al. (Evidence-Based Complementary and Alternative Medicine Volume 2017, Article ID 4380721) recently reported α-glucosidase inhibitory and antidiabetic effects of Nopal in low-dose streptozotocin-induced diabetic rats fed a high-fat diet, thus indicating it could be considered as a dietary supplement for the prevention and/or treatment of T2DM.

Notably, its mucilage rich composition in polyphenols, vitamins, polyunsaturated fatty acids and amino acids has been highlighted through the use of a large panel of extraction methods. The identified natural cactus compounds and derivatives were shown to be endowed with biologically relevant activities including anti-inflammatory, antioxidant, hypoglycemic, antimicrobial and neuroprotective properties. In the last decade, compelling evidence for the nutritional and health benefit potential of Nopal has been provided by academic scientists and private companies (El-Mostafa K et al. Molecules 2014; 19:14879).

From the discussions above, the four natural ingredients from the plants and vegetable sources appear to be efficacious as adjunctive to our primary ingredients in Table 1. These are, therefore, compiled in Table 2, as mentioned below.

TABLE 2

| INGREDIENTS | AMOUNTS | RANGES |
| --- | --- | --- |
| Gymnema | 100 mg | 5-850 mg |
| Bitter Melon | 100 mg | 10-1000 mg |
| Okra | 100 mg | 5-700 mg |
| Nopal | 300 mg | 25-2000 mg |

Extracts of all of the four secondary ingredients in Table 2 are expected to function in synergy with our primary ingredients in Table 1 as adjunctive. The complete list of our new Nutrient Composition is, therefore, listed in Table 3, below.

TABLE 3

| INGREDIENTS | AMOUNTS | RANGES |
| --- | --- | --- |
| Goat's rue | 150 mg | 20-1,000 mg |
| Cinnamon | 225 mg | 30-1,800 mg |
| Gymnema | 100 mg | 5-850 mg |
| Bitter Melon | 100 mg | 10-1000 mg |
| Okra | 100 mg | 5-700 mg |
| Nopal | 300 mg | 25-2000 mg |

Using certain appropriate amount of each of the ingredients in Table 3, extracted following some important Proprietary Procedures, tablets were made to conduct the following human studies in order to verify the efficacies and to validate the use of this new Nutrient Composition. Doses were determined to be taken by mouth 2 tablets twice a day at least with two main meals, preferably at breakfast and at dinner.

BRIEF DESCRIPTION OF THE DRAWINGS

FIG. 1 shows the observed results of observations on Pre-diabetes.

1. ANECDOTAL OBSERVATIONS ON PRE-DIABETICS

A small group of pre-diabetic patients (n=10, F=4) was recruited in order to investigate initially if this Nutrient Composition of Table 3 is capable of controlling the IR, which is mainly responsible for initiating T2DM. This was done by supplementing 2 tablets of this new Nutrient Composition, twice a day with main meals, breakfast and dinner, to these pre-diabetic volunteers, for one month only. Three of these pre-diabetics were found to be obese, whose body mass index (BMI) was above 30 $kg/m^2$ and continue taking this supplement for another month. The base-line fasting blood sugar of these volunteers ranges between 100 and 126 mg/dL with higher level of insulin (hyperinsulinemia), which usually is indicative of IR in T2DM. The observed results are summarized in FIG. 1:

It could be observed in this FIGURE that after supplementing the Nutrient Composition for a month only, the fasting blood sugar level was lowered from 112±10 to 105±6 mg/dL. However, the insulin level was highly significantly (p<0.001) reduced from 23±5 (hyperinsulinemia) to the normal level of 11±4 mU/L. This is an extremely important observation suggesting strongly that this new nutrient Composition is indeed capable of controlling IR. Additionally, it was also observed as in FIG. 1 that those 3 obese volunteers showed a significant trend of loss of body weight. Thus this new Nutrient Composition is expected to be highly capable of not only preventing an onset of diabetes in pre-diabetics, but also perhaps as an anti-obese treatment, if taken for a longer period of time.

2. A RANDOMIZED CASE-CONTROL CLINICAL TRIAL ON T2DM PATIENTS

This randomized case-control clinical trial for the new Nutrient Composition (Supplement) on T2DM patients was conducted at a renowned diabetes treatment clinic. Twenty (n=20, F=10) T2DM, age, sex and duration of this disease matched, non-ambulatory patients were selected for this study. All of these patients were suffering from uncontrolled blood sugars with some health complications due to diabetes and were being treated with a combination of 3 or 4 hypoglycemic drugs, containing particularly Glucophage/Metformin, Glipizide and Pioglitazone. They were randomized to receive either the Supplement or the Placebo (containing methylcellulose), 2 tablets twice a day, at breakfast and dinner, for 3 weeks only. After completion, they were grouped as Placebo (controls) and Supplement (cases) as presented in the Table 4, below, along with their demographic and biochemical findings as analyzed statistically.

TABLE 4

Demographic and Biochemical Parameters

| Parameters | Supplement (n = 10) | Placebo (n = 10) | p-value |
| --- | --- | --- | --- |
| Sex | M = 5, F = 5 | M = 5, F = 5 | — |
| Age (years) | 46.6 ± 12.3 | 46.8 ± 11.8 | NS |
| Weight (kg) | 58.7 ± 10.6 | 58.5 ± 9.9 | NS |
| Height (cm) | 155.9 ± 5.8 | 156.1 ± 7.6 | NS |
| Race | Asian Indians | Asian Indians | — |
| Blood Sugars (mg/dL) | | | |
| Pre- | 244 ± 36.4 | 236.8 ± 30.6 | NS |
| Post- | 231.8 ± 12.6 | 243.2 ± 16.2 | <0.05 |
| TBARS (µmol/L) | | | |
| Pre- | 8.6 ± 1.3 | 8.7 ± 0.9 | NS |
| Post- | 6.5 ± 0.7 | 8.6 ± 0.8 | <0.001 |

It is clear in the table above that the blood glucose level in the Supplement group went down significantly (p<0.05). Because of short duration, 3 weeks only, the sugar level did not reach to the normal level, which possibly could have attained if the duration of treatment was longer. Inflammation in the diabetic patients as expected to be high, is also evident in the table above in terms of TBARS (Thiobarbituric Acid Reacting Substances). TBARS was reduced significantly (p<0.001) in the group taking Supplement, indicating thus a remarkable reduction of inflammation in the diabetic patients. This, therefore, provides strong evidence that the new Nutrient Composition of Table 3 is indeed a highly effective anti-inflammatory product, as expected, and also capable of controlling blood sugars.

The clinical observations, as described in Table 5 (below), clearly show that complications due to the metabolic disorders (hyperglycemia and heart conditions) were relieved and most importantly a tremendous feeling of wellness was observed, as reported by the supplemented patients. These observations validate the efficacies of our new Nutrient Composition in relieving many health complications in T2DM diabetics in addition to blood sugar reduction, and most importantly having no undesirable side-effects, as reported by the patients after taking the Supplement.

TABLE 5

Clinical Observations

| Patients | Health Complications | Clinical Outcomes |
| --- | --- | --- |
| Female, age 48 years | Uncontrolled blood sugar, diabetic-nerve pain on foot and fatigue | Blood sugar started getting lower, foot pain diminished and gained a considerable energy. |

TABLE 5-continued

Clinical Observations

| Patients | Health Complications | Clinical Outcomes |
| --- | --- | --- |
| Male, age 55 years | Uncontrolled blood sugar, sign of cataract formation in both eyes and erectile dysfunction. | Blood sugar controlled, energized and an improved sexual health, a diminished sign of cataract formation |
| Male, age 44 years | Fatigue, diabetic neuropathy, skin lesions and uncontrolled blood sugar. | Sugar was under controlled; no sign of neuropathy, skin lesions were relieved considerably. |
| Male, age 59 years | Severe weight loss, numbness and tingling (neuropathy), arrhythmia and weakness | Sugar was lowered, arrhythmia and weight loss were controlled, neuropathy relieved, started feeling of wellness. |
| Female, age 46 years | Neuropathy in terms of burning sensation in the limbs, circulatory abnormality and cold sweat | A considerable improvement in blood circulation, no more burning sensation and cold sweating. |
| Female, age 54 years | Cardiomyopathy (dilated with about 33% heart function) and severe weakness | Blood sugar showed improvement along with heart function and weakness was reduced remarkably |
| Female, age 45 years | Fatigue, weight loss, early sign of cataract | Blood sugar normalized, gained energy and improved weight and eye sight |
| Male, age 47 years | Uncontrolled blood sugars, cold sweat, arrhythmia and general weakness | Most of this patient's health conditions improved and his quality of life improved. |
| Male, age 50 years | Neurological problems due to uncontrolled blood sugar, unable to walk without a support and had an old untreatable wound near his right ankle. | Blood sugar was lowered significantly, although not to the normal range. But his old wound healed completely and he started walking without a support, a remarkable case of recovery. |

3. EFFECTS ON PERIPHERAL NEUROPATHY

As observed in the clinical findings in Table 5 above, a couple of patients indicated a greater relief of their diabetic nerve pain. Since this diabetic nerve pain, a peripheral neuropathy, has been reported (http://www.painmed.org/library/research/neuropathic) to pose a greater threat to the quality of life of many T2DM patients, we tested the efficacy of our new Nutrient Composition on some severely affected T2DM patients with diabetic nerve pain being treated by an experience neurologist as illustrated below.

Case #1. 76-year-old Asian Origin American female has a history of diabetes for many years, taking Metformin, she also has hypertension, knee pain and knee replacement. She complains of having tingling and numbness in her legs and feet and in drawing and twisting of legs for more than a year. Sometimes she gets in drawing and cramps and spasm of leg muscles at night. She had to cry and literally her grandchild had to sit on her feet to keep it straight. Patient was started taking the Supplement, which is a complementary support for blood sugar. She started taking 2 tablets twice a day as recommended. In one week, she started feeling good. After 2 weeks she had dramatic improvement in her leg cramps, she did not have any further leg cramps and had only one episode in a month and her tingling sensations had also improved. Since we did not monitor her for a longtime, we didn't check for HgA1c. Her regular blood sugar levels also seem to be controlled. She was on Metformin for a long time. We feel at this time that the Supplement contributed to her better blood sugar control. Diabetes itself can cause neuropathy with symptoms of muscle cramps; and treatment with Metformin has also shown to cause neuropathy itself. It is suggested that this Supplement, which helped control her blood sugar with beneficial effects on neuropathy, should be taken along with Metformin to achieve the treatment goals.

Case #2. 82-year-old Caucasian American female has a long-standing history of diabetes, hypertension, and anxiety disorder. She presented with complaints of having burning sensation in her legs and also to her hands for a while. She could not sleep well because of this burning sensation and she had been anxious because of the discomfort for a while. She was prescribed the Supplement, which she took 2 tablets twice a day as recommended. At the end of 2 weeks she started feeling much comfortable, her burning and tingling sensations had moderately improved. She had been sleeping well and she was less anxious. She has been taking Alprazolam for longtime because of the anxiety from the feeling of discomfort in her legs and feet and she could not sleep. As reported by her and her husband, she had been sleeping well, doing better since she started the Supplement. Her blood sugar had been fluctuating since she was not compliant on her Metformin and sometimes she had to take Insulin. It is the Supplement that has contributed for her better control of blood sugar, which was encouraging and easier for her to take the pills and it also helped her relieve some of her symptoms of neuropathy.

Case #3. 65-year-old Caucasian female came to the clinic with her husband. She has a history of hypertension, diabetes, and depression for a longtime. She presented with complaints of having pain and cramps in her legs and feet for more than a year and she could not sleep well. She was prescribed the Supplement, which she took for a few days. However, she says she started having diarrhea-like symptoms and she discontinued the Supplement. It is not sure if the Supplement caused this diarrhea-like symptom or she had it because of other reasons. So, in this case we could not draw any conclusion on the efficacy of the Supplement.

Case #4. 58-year-old African American male came to the clinic alone. He has a history of diabetes, hypercholesterolemia for a few years. He had complained of burning sensation in both his feet and legs for 6 months and he had been taking oral hypoglycemic agents, Metformin, for more than a year. He also continued to have night cramps. He was prescribed the Supplement and he reported a moderate improvement of his symptoms of neuropathy and leg cramps in 3 weeks. He didn't have any side effects from the Supplement.

Case #5. 66-year-old African American female has a history of hypertension, diabetes, hypercholesterolemia, and depression. She says she controls her blood sugar with hypoglycemic agents, she did not need Insulin. She presented with complaints of difficulty sleeping at night because of feeling of restlessness in her legs. She also complained of burning and tingling sensation and cramps in her legs, which interfered with sleeping at night and she felt tired during the daytime. She was prescribed the Supplement and within 3-4 weeks, she reported moderate benefit of her symptoms of leg cramps and burning sensation in her feet. Her blood sugar by finger stick was also well-controlled on taking this Supplement.

By monitoring and reviewing the symptoms of these patients for about two months, it could be concluded that the new Nutrient Composition has indeed many beneficial effects in controlling at least some peripheral neuropathy and leg cramps.

As elaborated above, diabetes is responsible for many life threatening complications to human health. Although the incidence of Type 1 diabetes (T1D), also known as insulin dependent diabetes mellitus (IDDM), is much less, about 5 to 10% of the total of T1D and T2DM, the number of T2DM also known as non-insulin dependent diabetes (NIDDM) patients is steadily increasing worldwide. The number of pre-diabetics is almost 3 times more than diabetics. For example, number of diabetics currently is about 30 million, whereas the number of pre-diabetics is around 100 million in the USA; in China there are about 120 million diabetics and more than 350 million pre-diabetics and in the Indian subcontinent the number of diabetics is over 150 million, with almost 1 in 3 as pre-diabetics (Forouhi N G and Wareham N J. Medicine 2014; 42:698). The number of pre-diabetics is, however, increasing in an alarming rate, which may be reaching to a billion marks worldwide sooner than later.

It has been observed in this disclosure that after supplementing the new Nutrient Composition of Table 3, for a month only, that the fasting blood sugar level was lowered from a total average of 6.2 mmol/L (112 mg/dL) to 5.8 mmol/L (104 mg/dL), while the insulin level was statistically significantly (p<0.001) reduced from 22 (hyperinsulinemia) to the normal level of 8.9 mU/L, thus indicating that this Nutrient Composition is indeed capable of controlling insulin resistance (IR), a hallmark of a person becoming diabetic sooner or later. This is an extremely important observation, since this Composition is very likely be capable of preventing onset of diabetes in pre-diabetics. Another important observation could be noted in the present findings, as stated above, that the body weight of obese patients was found to be reduced, indicating another use of this Composition to control obesity.

Inflammation, as mentioned earlier, has been found to be associated with many human health complications, particularly diabetes and cardiovascular diseases (CVD). Postprandial inflammation, provoked soon after ingesting a meal, is transient in duration, but with dreadful consequences on human health over a period of time depending on the compositions of a meal. However, many populations, particularly obese people, are in a constant postprandial state, which is likely to initiate insulin resistance (IR) resulting in T2DM and CVD. Postprandial inflammation is dependent on the food quality and quantity, mostly in terms of its energy/calorie content and its nutritional value. Micronutrients, such as minerals and vitamins, constitute the nutritional value of a food, while macronutrients, such as carbohydrate, protein and fat/lipid, are basically the sources of its energy/calorie content. The inventor, Khaled M A, and coworkers have previously revealed that postprandial inflammation occurs 2 hours after consuming a meal, either high in carbohydrates or high in fat/lipid (http://www.gscience.com/doi/pdf/10.5339/qfarf.2012.BMP69). It has also been cited earlier that glucotoxicity is induced by consuming carbohydrates, while fat/lipid is primarily responsible for lipotoxicity. Our new Nutrient Composition, as designed to prevent these gluco- and lipotoxicities to control the occurrence of IR, has been shown to be successful in this respect in a randomized case-control study on T2DM patients, as presented above. Patients in this study were suffering from an uncontrolled sugar level even after taking several hypoglycemic prescription drugs and also having various sugar related health complications. Inspection of Table 4 clearly shows that the sugar level was statistically significantly (p=<0.05) lower in the supplemented group compared to the control group. Inflammation, in terms of TBARS, was also highly significantly (p=<0.001) lower (see Table 4) after taking the Composition just for 3 weeks only. This suggest that a desirable benefit by using this Composition may be expected if taken for an extended period of time. Clinical outcomes after consuming this Composition indicate a greater relief from many of their health complications as listed in Table 5. While metabolic syndromes, in terms of T2DM and CVD, were much improved, peripheral neuropathy due to uncontrolled blood sugars in a couple of these patients was also noticed. A separate anecdotal observation was, therefore, performed to verify the efficacy of this new Nutrient Composition on 5 patients suffering from various diseases, mostly from diabetic nerve disorders. Except one patients, all 4 completed this study, conducted for 2 months. A tremendous beneficial effects due to this Composition were reported back to us by these patients, as described above.

The above mentioned results, although conducted on a small number of T2DM patients all together, suggested strongly that the new Nutrient Composition could potentially improve metabolism in both the pre-diabetes and T2DM patients, through its effects to reduce/reverse the insulin resistance (IR). These small studies and anecdotal experiences, and the rational construction of the Composition itself, may extend its further use for patients with Type 1 diabetes, for people suffering from peripheral neuropathy, for people with heart diseases and perhaps most importantly for obese people to improve insulin sensitivity and glucose homeostasis, concomitantly losing some body weight.

The invention claimed is:

1. A tableted composition in an oral dosage form comprising:
    A) 30-1800 mg of a Cinnamon product selected from cinnamon oil, cinnamon extract, ground cinnamon and combinations thereof,
    B) 20-1000 mg of an extract from the Fabaceae family selected from Goat's Rue extracts, Fenugreek oil extracts and combinations thereof,
    C) 5-850 mg of an extract of gymnema, or *Momordica charantia*, and
    D) 5-700 mg of an extract of *Abelmoschus esculentus* or *Opuntia ficus-indica*.

2. The tableted composition of claim 1 wherein the extract of gymnema is selected as component C and an extract of *Opuntia ficus-indica* is selected as component D, said tableted composition additionally comprising:
    E) 10-1000 mg of an extract of *Momordica charantia*, and
    F) 25-2000 mg of an extract of *Abelmoschus esculentus*.

3. The tableted composition of claim 2 which comprises
    50-500 mg of the Cinnamon product,
    50-500 mg of the extract from the Fabaceae family,
    50-500 mg of an extract of gymnema,
    50-500 mg of an extract of *Opuntia ficus-indica*,
    50-500 mg of an extract of *Momordica charantia*, and
    50-500 mg of an extract of *Abelmoschus esculentus*.

4. The tableted composition of claim 3 wherein the cinnamon product is provided in a range of 50 mg and 300 mg.

5. The tableted composition of claim 3 wherein the extract from the Fabaceae family is provided in a range from 50 mg to 300 mg.

6. The tableted composition of claim 3 wherein the extract of gymnema is provided in a range from 50 mg to 300 mg.

7. The tableted composition of claim 3 wherein the extract of *Opuntia ficus-indica* is provided in a range from 50 mg to 300 mg.

8. The tableted composition of claim 3 wherein the extract of *Momordica charantia* is provided in a range from 50 mg to 300 mg.

9. The tableted composition of claim 3 wherein the extract of *Abelmoschus esculentus* is provided in a range from 50 mg to 300 mg.

10. The tableted composition of claim 2 wherein the cinnamon product is cinnamon extract, the extract from the Fabaceae family is Goat's Rue extract.

11. The tableted composition of claim 1 wherein the extracts are alcohol extracts.

12. A tableted composition in an oral dosage form comprising:
   A) About 225 mg of a cinnamon extract,
   B) About 150 mg of Goat's Rue extract,
   C) About 100 mg of gymnema extract,
   D) About 100 mg of an extract of *Abelmoschus esculentus*,
   E) About 100 mg of an extract of *Momordica charantia*, and
   F) About 300 mg of an extract of *Opuntia ficus-indica*
   wherein "about" is variation of from 0% to 5% of the value indicated.

* * * * *